United States Patent [19]

Bowman et al.

[11] Patent Number: 5,304,688
[45] Date of Patent: Apr. 19, 1994

[54] PROCESS FOR THE PREPARATION OF BISHYDROXY AROMATIC COMPOUNDS

[75] Inventors: Robert G. Bowman; Muthiah N. Inbasekaran, both of Midland, Mich.

[73] Assignee: The Dow Chemical Company, Midland, Mich.

[21] Appl. No.: 46,696

[22] Filed: Apr. 13, 1993

[51] Int. Cl.$^5$ ............................................. C07C 39/16
[52] U.S. Cl. .................................. 568/727; 568/717; 568/722; 568/723
[58] Field of Search ............... 568/718, 721, 727, 722, 568/720

[56] References Cited

U.S. PATENT DOCUMENTS

| | | | |
|---|---|---|---|
| 3,496,239 | 2/1970 | Hamilton et al. | 260/619 |
| 4,467,122 | 8/1984 | Szabolcs | 568/727 |
| 4,675,458 | 6/1987 | Riemann et al. | 568/727 |
| 4,931,594 | 5/1990 | Knebel et al. | 568/727 |
| 5,001,281 | 3/1991 | Li | 568/727 |
| 5,008,470 | 4/1991 | Powell et al. | 568/727 |
| 5,110,994 | 5/1992 | Fialla | 568/727 |
| 5,149,886 | 9/1992 | Orth et al. | 568/727 |
| 5,169,990 | 12/1992 | Orth et al. | 568/727 |

OTHER PUBLICATIONS

P. W. Morgan, *Macromolecules,* vol. 3, 536 (1971).
CA 82:112410h (1975).
CA 101:6822v (1984).
CA 104:224699p (1986).
CA 114:206760d (1991).
Makoto Hino et al., *Journal of the American Chemical Society,* vol. 101, 6439 (1979).
Makoto Hino et al., *Journal of the Chemical Society,* Chemical Communications, 851 (1980).
Makoto Hino et al., *Journal of the Chemical Society,* Chemical Communications, 1148 (1979).
K. Tanabe et al., *Critical Reviews of Surface Chemistry,* vol. 1, 1 and 21-23 (1990).
K. Arata, *Advances in Catalysis,* Solid Superacids, vol. 37, 165-211 (1990).

*Primary Examiner*—Werren B. Lone
*Attorney, Agent, or Firm*—Marie F. Zuckerman

[57] ABSTRACT

A process for the preparation of bishydroxy aromatic compounds, such as 9,9-bis(4-hydroxyphenyl)fluorene, involving contacting a ketone, such as fluorenone, with phenol or substituted phenol in the presence of a mercaptan cocatalyst and a solid superacid catalyst of Hammett acid strength $H_0$ greater than about $-13.0$. Solid superacid catalysts include the sulfates, sulfated oxides, sulfated oxyhydroxides, and sulfated oxysilicates of aluminum, tin, and the Group IVA metals, such as zirconium, as well as mixed metal oxides, such as tungsten-zirconium oxides. Isolated yields are high for 9,9-bis(4-hydroxyphenyl)fluorene.

20 Claims, No Drawings

PROCESS FOR THE PREPARATION OF BISHYDROXY AROMATIC COMPOUNDS

BACKGROUND OF THE INVENTION

This invention pertains to a process for the preparation of bishydroxy aromatic compounds.

Bishydroxy aromatic compounds, such as 9,9-bis(4-hydroxyphenyl)fluorene and 2,2-bis(4-hydroxyphenyl)propane (bisphenol-A), are useful monomers for preparing polycarbonates, polyesters and polyethers.

P. W. Morgan discloses in *Macromolecules*, 3, 536 (1971) the acid-catalyzed phenolation of aromatic and alkaryl ketones to bishydroxy aromatic compounds. For example, it is taught that fluorenone reacts with molten phenol in the presence of 3-mercaptopropionic acid and gaseous hydrochloric acid to yield 9,9-bis(4-hydroxyphenyl)fluorene.

U.S. Pat. No. 4,467,122 discloses the phenolation of aromatic ketones to bishydroxy aromatic compounds in the presence of gaseous hydrogen halide and at least one divalent, trivalent or tetravalent metal halide wherein the metal is selected from Groups IIA, IIB, IIIA, IVA, IVB, and VIIIB of the Periodic Table. For example, fluorenone is reacted with phenol in the presence of zinc chloride and gaseous hydrogen chloride to yield 9,9-bis(4-hydroxyphenyl)fluorene.

One disadvantage of the aforementioned processes is that hydrochloric acid and metal halides are corrosive to the metal equipment used in an industrial-scale process.

U.S. Pat. No. 4,675,458 teaches the phenolation of fluorenone to 9,9-bis(4-hydroxyphenyl)fluorene in the presence of sulfuric acid and a thiol promoter. Disadvantageously, the concentration of the sulfuric acid must be greater than 75 weight percent, preferably 85 to 100 percent, and the acid must be neutralized on workup resulting in a waste problem. As a further disadvantage, the operating temperature must be maintained between about 20° C. and 70° C. to minimize sulfonated byproducts, thus requiring long reaction times.

More recently, U.S. Pat. No. 4,931,594 discloses the condensation of diaryl ketones, such as fluorenone, with phenols in the presence of acidic cation exchange resins to form aromatic bisphenol compounds. The ion exchange resins which are suitable are taught to include macroporous sulfonated crosslinked polystyrenes and the corresponding styrene/acrylate copolymers, or poly(perfluoroalkylene)sulfonic acid. Disadvantageously, the process requires high temperatures and the yield of the desired 4,4'-isomer of 9,9-bis(hydroxyphenyl)fluorene, is only 60 to 75 mole percent.

In view of the above, it is clear that a need exits to find a process for preparing bishydroxy aromatic compounds in high selectivity and yield of the desired isomer and without corrosion and waste problems.

SUMMARY OF THE INVENTION

This invention is a process of preparing bishydroxy aromatic compounds comprising contacting a ketone with unsubstituted or substituted phenol in the presence of a solid superacid catalyst and a mercaptan cocatalyst. The solid superacid catalyst is selected from the group consisting of metal sulfates, sulfated metal oxides, sulfated metal oxyhydroxides, sulfated metal oxysilicates, superacid metal oxides, and mixtures thereof. The aforementioned solid superacid catalysts are required to have an acid strength $H_0$ stronger than about $-13.0$. The contacting of the ketone with the phenol is conducted under reaction conditions such that a bishydroxy aromatic compound is formed.

The process of this invention is useful for preparing bishydroxy aromatic compounds, such as bisphenol-A and 9,9-bis(4-hydroxyphenyl)fluorene, which may be employed as monomers for the preparation of useful polymers. Advantageously, the process of this invention produces fewer unwanted by-products. For example, the selectivity and yield of the desirable 4,4'-isomer of the aforementioned products is high. More advantageously, the process of this invention does not require hydrochloric or sulfuric acid. Accordingly, this process is not corrosive, does not require a neutralization step, and does not produce a waste salt stream. As a further advantage, the solid superacid catalyst employed in this process is easily separated from the product stream and easily regenerated.

DETAILED DESCRIPTION OF THE INVENTION

In accordance with the process of this invention, an aliphatic, alicyclic, alkaryl, or aromatic ketone is contacted with a substituted or unsubstituted phenol in the presence of a solid superacid catalyst, described hereinafter and characterized as having a Hammett acid strength $H_0$ stronger than about $-13.0$, and a mercaptan cocatalyst to yield a bishydroxy aromatic compound. In a preferred embodiment of this invention, phenol is contacted with fluorenone in the presence of the aforementioned catalyst and cocatalyst to yield 9,9-bis(4-hydroxyphenyl)fluorene in high yield.

Phenols suitable for the process of this invention include unsubstituted phenol and substituted phenols, provided that the substituent or substituents do not interfere with the condensation process of this invention. Alkyl, aryl, aralkyl, and alkaryl substituents are all suitable, as are halo substituents. Cyano and nitro substituents, however, may be too deactivating, and carboxylic acid and aldehyde substituents may interfere with the condensation process via reaction with the phenol. Hydroxyl substituents may be suitable in some cases, while in other cases their reactivity may complicate the formation of desired products. Preferred substituents include alkyl moieties containing from 1 to about 10 carbon atoms, more preferably, lower alkyl moieties, such as those containing from 1 to about 5 carbon atoms, and most preferably, from 1 to 3 carbon atoms. The substituent or substituents are suitably located on the ortho and/or meta positions relative to the hydroxyl moiety. The para position relative to the hydroxyl moiety must remain free, because it is this position which participates in the condensation process of the invention. Preferably, one or both ortho positions are substituted. Non-limiting examples of suitable substituted phenols include o-cresol, m-cresol, o- or m-cumenol, 2,6-dimethylphenol, 2-methyl-6-ethylphenol, 2-chlorophenol, 2-bromophenol, 2-fluorophenol, 2,3,6-trimethylphenol, 2,3,5,6-tetramethylphenol, 2,6-dichlorophenol, 2,6-di-t-butylphenol, o-phenylphenol, 2,6-diphenylphenol, 3,5-dimethylphenol, 3,5-diethylphenol, and o-benzylphenol. Preferably, the phenol is unsubstituted phenol or phenol substituted at the ortho position(s) with an alkyl moiety of from 1 to about 5 carbon atoms. More preferably, the phenol is unsubstituted phenol.

Any aliphatic, alicyclic, alkaryl, or aromatic ketone is suitable for the process of this invention so long as it shows a measurable level of activity in the condensation process of this invention. Non-limiting examples of suitable ketones include acetone, methyl ethyl ketone, diethyl ketone, methyl isopropyl ketone, methyl isobutyl ketone, acetophenone, ethyl phenyl ketone, cyclohexanone, cyclopentanone, benzophenone, fluorenone, indanone, anthraquinone, acenaphthene quinone, and the like. Ketones substituted with halo, nitrile, nitro, and ester functionalities are also suitable, an example of a halo substituted ketone being 1,3-dichloroacetone. Carboxylic acid and aldehyde functionalities are usually not suitable because of the reactivity of these functionalities with phenol. Preferably the ketone is an aromatic ketone, more preferably an unsubstituted or substituted fluorenone represented by the structure:

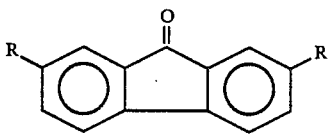

wherein each R independently may be hydrogen, an alkyl moiety having from 1 to about 5 carbon atoms, such as methyl, ethyl and the like; or a halo moiety, such as chloro, bromo, or fluoro. Most preferably, each R is hydrogen, and the ketone is fluorenone.

Any molar ratio of the phenol to ketone is acceptable provided that a bishydroxy aromatic compound is formed as the predominant product in the process of this invention. Typically, the molar ratio of phenol to ketone ranges from 2 to about 40. Preferably, the molar ratio of phenol to ketone ranges from 3 to about 20, more preferably, from 4 to about 10, and most preferably, from 4 to about 8. Below the lowest typical ratio of 2, by-product formation may increase. For example, the product bishydroxy aromatic compound may react at a free ortho position with excess ketone to yield higher condensation products. Above the highest typical ratio of 40, the separation and disposal of a large excess of phenol may be expensive and problematical.

When unsubstituted phenol is a reactant in the process of this invention, the process may be conducted in molten phenol without the further addition of solvent. Substituted phenols having melting points below about 180° C. may also be used in a neat, molten phase. However, it may be desirable in certain circumstances to conduct the process of this invention in the presence of a solvent, and such will be the case when the phenol has a melting point above about 180° C. Any solvent is suitable provided that it does not adversely interfere with the process of this invention. Acceptable solvents include, for example, chlorinated benzenes, such as chlorobenzene, o-dichlorobenzene, and trichlorobenzene, as well as alkylated benzenes, such as toluene, xylenes, ethylbenzene, and the like. The amount of solvent employed usually ranges from about 100 ml to about 1 liter per mole of ketone used, preferably from about 200 ml to about 400 ml per mole of ketone used.

To increase the reaction rate of the process, mercaptans are added as cocatalysts. Mercaptans having from 1 to about 12 carbon atoms and, optionally, substituted with certain functionalities, such as hydroxyl, carboxyl or sulfonic acid moieties, are suitable. Suitable mercaptans include, for example, ethylmercaptan, n-butylmercaptan, 1-octylmercaptan, 1-dodecylmercaptan, mercaptoethanol, mercaptoacetic acid, mercaptopropionic acid, mercaptoethanesulfonic acid, and mercaptopropanesulfonic acid. Preferably, the cocatalyst is a mercaptocarboxylic acid, more preferably, 3-mercaptopropionic acid. The mercaptans are used in an amount from about 0.002 to about 0.5 mole mercaptan per mole ketone, preferably, from about 0.004 to about 0.2 mole mercaptan per mole ketone. In a preferred mode of operation involving the condensation of fluorenone with a phenol, 3-mercaptopropionic acid is added in an concentration between about 0.005 and 0.1 mole per mole fluorenone.

The catalyst which is employed in the process of this invention is an inorganic, non-zeolitic, solid superacid having an acid strength $H_0$ stronger than about $-13.0$. The term "inorganic" is meant in its usual sense to include compounds other than those containing carbon. The term "non-zeolitic" is meant to include compounds other than crystalline, microporous aluminosilicates. Since the catalyst is a solid and essentially insoluble in the reaction and product streams, the catalyst is heterogeneous. Accordingly, the catalyst is easily separated from the product stream. Since the catalyst possesses a surface acidity which is stronger than the acidity of 100 percent sulfuric acid, the catalyst employed in the process of this invention is considered to be a "superacid." The acid strength $H_0$ of 100 percent sulfuric acid is estimated to be $\leq -11.9$ (G. A. Olah et al., *Science*, 1979, 206, 13). The measurement of acid strength is discussed in detail hereinbelow.

Solid superacids which are suitable for the process of this invention include metal sulfates, sulfated metal oxides, sulfated metal oxyhydroxides, and sulfated metal oxysilicates, as well as, superacid metal oxides, all being characterized as having an acid strength $H_0$ stronger than about $-13.0$. Preferred solid superacids which are suitable for the process of this invention include sulfates, sulfated oxides, sulfated oxyhydroxides, and sulfated oxysilicates of aluminum, tin, and the Group IVA metals, namely titanium, zirconium, and hafnium. Non-limiting examples of such preferred catalysts include titanium sulfate, zirconium sulfate, hafnium sulfate, aluminum sulfate, tin sulfate, sulfated titania, sulfated zirconia, sulfated hafnia, sulfated alumina, sulfated tin oxide, sulfated titanium oxyhydroxide, sulfated zirconium oxyhydroxide, sulfated aluminum oxyhydroxide, sulfated titanium oxysilicate, sulfated zirconium oxysilicate, and the like. Other preferred solid superacids include superacid mixed metal oxides, such as tungsten-zirconium oxides, molybdenum-zirconium oxides, tungsten-titanium oxides, and molybdenum-titanium oxides. Mixtures of any of the above-identified solid superacids are also acceptable. The more preferred solid superacid catalysts include zirconium sulfate, sulfated zirconium oxide, sulfated zirconium oxyhydroxide, sulfated zirconium oxysilicate, tungsten-zirconium oxides, and zirconium sulfate supported on a suitable support as noted hereinbelow.

The metal sulfates are available commercially and may be activated by heating under air at a temperature between 300° C. and 700° C. for several hours. The preparation of the sulfated oxides, oxyhydroxides, and oxysilicates comprises treating a precursor metal oxide, oxyhydroxide or hydroxysilicate with a source of sulfate and thereafter calcining the treated precursor under conditions such that sulfate moieties chemically bind to the surface of the precursor compound. Typically, the concentration of sulfur in the sulfated catalyst ranges from about 0.5 to about 12 weight percent, based on total catalyst weight.

Preferred precursor metal oxides which are suitable include zirconia, titania, and alumina. Oxyhydroxides of zirconium, titanium, and aluminum are also preferred precursor compounds. As the name indicates, the oxyhydroxides are oxides whose surfaces are hydroxylated. Oxyhydroxides can be purchased commercially as in the case of boehmite alumina. Alternatively, oxyhydroxides can be prepared simply by exchanging a metal salt containing an exchangeable anion with hydroxide. Such metal salts include metal oxides, metal halides, metal oxyhalides, and metal oxynitrates. Illustrative, but non-limiting, examples include zirconium oxychloride, titanium oxychloride, aluminum chloride, and zirconium oxynitrate. Typically, the exchangeable salt is slurried with an aqueous solution of ammonium hydroxide or alkali metal hydroxide in a ratio ranging generally from about 1 to about 25 moles hydroxide per mole exchangeable anion. The temperature and time that the salt is slurried in the basic solution is sufficient to effect nearly complete exchange. Usually, the temperature ranges from ambient, taken as about 22° C., to about 100° C., preferably from about 40° C. to about 80° C.

In addition to oxides and oxyhydroxides, oxysilicates, such a zirconium oxysilicate, are suitable precursor compounds. Oxysilicates may be prepared by reacting a salt of aluminum, tin or a Group IVA metal containing an exchangeable anion with an aqueous solution of an alkali metal silicate. For example, zirconium oxychloride will react with sodium silicate in aqueous solution to yield a precipitate of zirconium oxysilicate. Generally, the ratio of moles of silicon per mole zirconium or titanium salt ranges from about 0.1 to about 100. Again, the temperature ranges from about 22° C. to about 100° C., preferably, from about 40° C. to about 80° C.

As noted hereinbefore, the oxides, oxyhydroxides, and oxysilicate precursor compounds are treated with a source of sulfate to obtain the sulfated superacid catalyst. Typical sources of sulfate include sulfuric acid, diammonium sulfate, ammonium bisulfate, sulfonic acid, and sulfur trioxide, as well as aqeuous zirconium sulfate and aqueous titanium sulfate. In a typical procedure, the precursor oxide, oxyhydroxide or oxysilicate is immersed in an aqueous solution of sulfuric acid, stirred, filtered, and then dried and calcined. Any concentration of sulfuric acid is suitable which gives rise to the sulfated superacid catalyst of this invention. Typically, the concentration of acid ranges from about 0.1N to about 10N, preferably, from about 0.5N to about 2N. Likewise, any ratio of acid solution to precursor compound is acceptable provided that the sulfated superacid catalyst is achieved. Typical ratios range from about 1 ml to about 50 ml acid solution per gram precursor compound, preferably from about 3 ml to about 25 ml solution per gram precursor compound. The precursor compound is stirred with the acid solution for a time between about 0.5 hour and 5 hours. Afterwards, the sulfated precursor compound is filtered from the solution, dried at a temperature between about 80° C. and 120° C. to remove water, and calcined for at least about 3 hours at a temperature between about 250° C. and 800° C., preferably, between about 450° C. and 700° C., so as to bind chemically the sulfate moieties to the surface of the precursor compound. It is believed that free sulfate reacts with hydroxyls on the surface of the precursor compound to yield a sulfate moiety chemically bound to the metal oxide or silicate lattice, i.e. M—O—SO$_2$OH or M—O—Si—O—SO$_2$OH. Such a theory, however, should not be binding on the process of this invention.

The mixed-metal oxide superacid catalysts are prepared by physically mixing the individual oxide components and calcining the mixture, or alternatively, by impregnating one of the metal oxides with a solution containing the second metal oxide.

Optionally, the aforementioned solid superacids may be supported on alumina or a Group IVB metal oxide, preferably, zirconia or titania. For example, zirconium sulfate supported on zirconia, titania or alumina is a preferred supported solid superacid catalyst. Impregnation techniques, well known in the art, are useful for supporting the solid super acid on the metal oxide support.

According to K. Arata ("Solid Superacids," *Advances in Catalysis*, Volume 37, Academic Press, Inc., 1990, pp. 166–167), the acid strength of a solid is defined as the ability of the surface to convert an adsorbed neutral base into its conjugate acid. If the reaction proceeds by means of proton transfer from the surface to the adsorbate, the acid strength is expressed by the Hammett acidity function $H_0$:

$$H_0 = pK_a + \log [B]/[BH^+]$$

wherein [B] and [BH+] are, respectively, the of neutral base (basic indicator) and its conjugate acid, and $pK_a$ is $pK_{BH+}$.

The Hammett acidity function $H_0$ of solid superacids may be measured by observing color changes of Hammett acid-base indicators adsorbed on the surface of the solid. In the Hammett method, described by K. Arata, op. cit, as well as Makoto Hino et al., Journal of the American Chemical Society, 101, (1979) 6439, the solid superacid is suspended in powder form in an organic nonpolar solvent to which a Hammett acid-base indicator is added. Non-polar organic solvents are acceptable, but may be problematical. For example, the solid superacid may appear colored in standard non-polar organic solvents, thereby interfering with the observation of a color change in the indicator. Sulfuryl chloride and cyclohexane have been found to be suitable solvents for most systems to be tested. Hammett indicators which are available for the acidity measurement include, but are not limited to, p-nitrotoluene ($pK_a - 11.35$), p-nitrochlorobenzene ($pK_a - 12.70$), m-nitrochlorobenzene ($pK_a - 13.16$), 2,4-dinitrotoluene ($pK_a - 13.75$), 2,4-dinitrofluorobenzene ($pK_a - 14.52$), and 1,3,5-trinitrobenzene ($pK_a - 16.04$). Typically, the base form is colorless, whereas the acid form is yellow. Based upon the varying pKa's of the indicators, an observation of a color change to the acid form of the indicator or the absence of such a change yields a measure of the acid strength $H_0$ of the solid surface. As $H_0$ decreases in the direction of larger negative numbers, acid strength increases.

Estimates of the acid strength $H_0$ of the solid superacids identified hereinabove are available. For example, the acid strength $H_0$ of sulfated zirconium oxyhydroxide, calcined at a temperature of about 500° C., is estimated to be $\leq -14.52$ (M. Hino et al., Journal of the American Chemical Society, 101, (1979) 6439); sulfated zirconium oxyhydroxide, calcined at a temperature less than or about 650° C., $H_0 \leq -14.52$ (M. Hino and K. Arata, Journal of the Chemical Society-Chemical Communications, 1980, 851); sulfated zirconia, calcined at a temperature less than or about 650° C., $H_0 \leq -16.04$ (M. Hino and K. Arata, Journal of the Chemical Society-Chemical Communications, 1980, 851); sulfated titania, calcined at a temperature less than or about 525° C., $H_0 \leq -14.52$ (M. Hino and K. Arata, Journal of the Chemical Society-Chemical Communications, 1979, 1148); sulfated zirconium oxysilicate, $H_0 \leq -13.2$ (K. Tanabe et al., Critical Reviews in Surface Chemistry, 1(1), (1990) 1–25); sulfated alumina, $H_0$ between $-16.04$ and $-14.52$ (K. Arata, Advances in Catalysis, Vol. 37, Academic Press, Inc., 1990, p 186); zirconium sulfate, $H_0$ between $-13.60$ and $-12.70$ (K. Arata, Advances in Catalysis, op. cit., p 192); tungsten-zirconium oxide, $H_0 \leq -14.52$ (K. Arata, Advances in Catalysis, op. cit., p 202); and molydenum-zirconium oxide, $H_0 \leq -13.00$ (K. Arata, Advances in Catalysis, op. cit., p 203). All of the relevant portions of the above-identified citations are incorporated herein by reference.

In some instances, it may be difficult to measure the Hammett acidity function $H_0$ directly. Such an instance may occur when the solid to be evaluated gives a colored solution which interferes with the observation of a color change in the Hammett indicator. In these cases, it is possible to estimate acid strength $H_0$ indirectly by comparing the activity of the solid in question in alkane isomerization or hydrocarbon cracking processes with the activities in those processes of superacids of known acid strength. for example, solid superacids will typically isomerize butane and isobutane. The references previously cited of K. Arata, M. Hino et al., and K. Tanabe et al. provide details of these processes as a means of estimating acid strength, relevant portions of these references being incorporated herein by reference.

The solid superacid catalysts employed in the process of this invention typically possess an acid strength stronger than a Hammett indicator $H_0$ of about $-13.0$, preferably stronger than about $-14.5$, and more preferably, stronger than about $-15.5$.

The process of this invention can be conducted in any conventional reactor, including batch reactors, continuous flow reactors, and fluid transport reactors. A fixed-bed, continuous flow reactor is preferred in an industrial-scale setting.

Any operable temperature is acceptable for the process of this invention provided that a bishydroxy aromatic compound is formed as the predominant product. Typically, the temperature ranges from about 30° C. to about 200° C. Preferably, the temperature ranges from about 50° C. to about 150° C., more preferably from about 80° C. to about 120° C. Below the lowest typical temperature of about 30° C., the reaction rate may be too low. Above, the highest typical temperature of about 200° C., selectivity to the bishydroxy aromatic compound may decrease. Likewise, any operable pressure is suitable for the process of this invention provided that a bishydroxy aromatic compound is formed as the predominant product. Typical pressures can range from subatmospheric to superatmospheric. Preferred pressures range from about atmospheric to about 50 atm, more preferably, from about atmospheric to about 20 atm.

In a standard batch reactor, the contact time needed to effect almost complete conversion of the ketone will depend upon process conditions, such as, temperature and the molar ratio of reactants to catalyst and cocatalyst. When the preferred reaction conditions described hereinabove are employed, the contact time in a batch reactor rarely exceeds 5 hours. More often, the reaction is greater than 95 percent complete within one hour. In a continuous flow reactor, the contact time is determined by the liquid hourly space velocity, LHSV, measured as the volume of liquid feed passed per volume of catalyst per hour, or simply $hr^{-1}$. Typically, the liquid hourly space velocity falls between about $0.1\ hr^{-1}$ and about $10\ hr^{-1}$.

Eventually the solid superacid catalyst may lose activity by accumulation of too much water formed as a by-product in the process of this invention. Regeneration of the catalyst is simply conducted by heating the catalyst at a temperature between about 100° C. and 700° C. in the presence or absence of air for a time ranging from about 1 hr to 15 hr. The dried catalyst usually exhibits full activity.

When the unsubstituted or substituted phenol is contacted with the ketone, as described hereinabove, a bishydroxy aromatic compound is formed as the predominant product. Examples of such bishydroxy aromatic compounds include bisphenol-A formed by contacting phenol with acetone; 2,2-bis(4-hydroxyphenyl)-2-phenylethane formed by reacting phenol with acetophenone; and 9,9-bis(4-hydroxyphenyl)fluorene formed by contacting phenol with fluorenone. Preferably, the bishydroxy aromatic compound is represented by the structure:

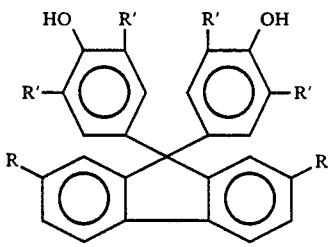

wherein each R is independently hydrogen, or an alkyl moiety having from 1 to about 5 carbon atoms or a halo moiety, and each R' is independently hydrogen or an alkyl moiety having from 1 to about 10 carbon atoms. More preferably, each R and R' is hydrogen, and the product is 9,9-bis(4-hydroxyphenyl)fluorene.

Isolation of the product from the reaction mixture involves the use of conventional techniques in most instances. For example, 9,9-bis(4-hydroxyphenyl)fluorene can be simply isolated from a crude product mixture containing the same, the corresponding 2,4-isomer, unreacted phenol, and catalyst. The crude product is dissolved in a conventional organic solvent, such as toluene, and thereafter the insoluble heterogeneous catalyst is filtered off. Water is added to the filtered solution to form an azeotropic mixture with phenol. The solution is rotary evaporated at which time the water-phenol mixture is removed and the toluene level is reduced. Crystal of the 4,4'-isomer precipitate from the residual solution and can be filtered off. Additional water may be added to the mother liquor, followed by further rotary evaporation to yield a second crop of 4,4'-isomer.

Conversion of the ketone in the process of this invention usually exceeds 90 mole percent. For the purposes of this invention conversion is defined as the mole percentage of ketone which is converted to form products. Conversion varies to some extent depending upon the specific reactants, process conditions, and form of the catalyst. At constant space velocity and pressure, conversion typically increases with increasing temperature. At constant temperature and pressure, conversion typically increases with decreasing space velocity. In the process of this invention, preferably, the conversion of the ketone varies from about 95 to about 99 mole percent.

The selectivity to the desired bishydroxy aromatic compound also varies as a function of the specific reactants, process conditions, and form of the catalyst. For the purposes of this invention, selectivity is defined as the mole percentage of converted ketone which forms a particular product, such as the bishydroxy aromatic compound. Generally, at constant pressure and space velocity, the selectivity decreases with increasing temperature. Conversely, at constant pressure and temperature, the selectivity usually increases with decreasing space velocity. Typically, the combined selectivity to all bishydroxy aromatic isomers is greater than about 95 mole percent, as determined by gas phase chromatography. In the preferred embodiment wherein the bishydroxy aromatic compound formed is 9,9-bis(hydroxyphenyl)fluorene, the selectivity to the 4,4'-isomer is usually greater than about 92 mole percent, and preferably, greater than about 96 mole percent, as determined by gas phase chromatography.

It is particularly desirable to achieve a high isolated yield of the 4,4'-isomer of the bishydroxy aromatic compound. Advantageously, the isolated yields of the 9,9-bis(4-hydroxyphenyl)fluorenes prepared by the process of this invention typically are greater than about 70 mole percent. Preferably, the isolated yield is equal to or greater than about 85 mole percent. More preferably, the isolated yield is about 90 mole percent.

The following examples are illustrative of the process of this invention, but are not intended to be limiting thereof.

Preparation of Sulfated Zirconium Oxyhydroxide Catalyst(E-1)

Zirconium oxychloride, $ZrOCl_2.4H_2O$, (100 g) is dissolved in 2 l of water in a 4 l stirred, baffle beaker and held at 70° C. Then, 1 l of 2N ammonium hydroxide is added to the zirconium oxychloride solution at a rate of 100 cc/min. The resulting mixture is stirred at 70° C. for 1 hr, then cooled overnight to room temperature, and filtered. The precipitate is washed three times with 2 l of distilled water until the washings give a pH of about 7. Then, the precipitate is dried at 110° C. overnight, the dried material being a zirconium oxyhydroxide. The oxyhydroxide is crushed and sieved to 24-40 mesh particles having a surface area of about 395 $m^2/g$.

Zirconium oxyhydroxide (20 g), prepared hereinabove, is immersed in 250 ml of 1N sulfuric acid and stirred for 1 hr. The treated solid is filtered and dried at 110° C. overnight. The dried solid is heated in air from 100° C. to 600° C. in 4 hr and then kept at 600° C. for 3 hr to yield a sulfated zirconium oxyhydroxide solid superacid catalyst, $[ZrO(OH)_2/SO_4]$. The catalyst contains 1 weight percent sulfur. The acid strength $H_0$ of sulfated zirconium oxyhydroxide is $\leq -14.52$. (M. Hino, Journal of the American Chemical Society, 101, (1979) 6439.)

Preparation of Sulfated Zirconium Oxide Catalyst (E-2)

Zirconium oxyhydroxide is heated in air at 300° C. for 3 hr to yield zirconium oxide. The zirconium oxide (10.6 g) is immersed in 120 ml of 1N sulfuric acid and stirred at room temperature for 1 hr. The resulting solid is filtered and dried at 110° C. overnight. The material is heated in air from 100° C. to 600° C. in 4 hr and then kept at 600° C. for 3 hr to yield a sulfated zirconium oxide solid superacid catalyst, $[ZrO_2/SO_4]$.

The acid strength $H_0$ of sulfated zirconium oxide is $\leq -16.04$. (M. Hino and K. Arata, Journal of the Chemical Society, Chem. Comm., 1980, 851.)

Preparation of Sulfated Zirconium Oxysilicate Catalyst (E-3)

A silicate solution is prepared by dissolving sodium silicate, $Na_2SiO_3.9H_2O$, (228 g) in 1.5 of water and heating to 80° C. Thereafter 50 cc of concentrated nitric acid are added to the sodium silicate solution slowly so that no precipitate is formed. The silicate solution is raised to 2 l volume with water. A zirconium solution is prepared by dissolving zirconium oxychloride, $ZrOCl_2.4H_2O$, (100.1 g) in 2 l of water in a stirred, baffle beaker at 80° C. The silicate solution is added to the zirconium solution at a rate of 100 cc/min, and the resulting mixture is heated for 2 hr at boiling. The precipitate which is formed is cooled to room temperature and filtered. The precipitate is washed three times with 2 l of water, dried overnight at 125° C., and then further dried at 300° C. for 4 hr to yield zirconium oxysilicate, $ZrOSi_2O_5$. A portion of the zirconium oxysilicate (4.4 g) is stirred in 60 ml of 1N sulfuric acid for 1 hr and filtered. The sulfate treated material is dried at 110° C. and calcined at 600° C. for 3 hr to yield a sulfated zirconium oxysilicate solid superacid catalyst, $ZrOSi_2O_5/SO_4$. The acid strength $H_0$ of sulfated zirconium oxysilicate is $\leq -13.2$. (K. Tanabe et al., Critical Reviews in Surface Chemistry, 1(1), (1990) 1.)

Preparation of Sulfated Titanium Oxide Catalyst (E-4)

Titanium oxide is prepared by adding titanium t-butoxide (100 g) to 2 l of water. The volume of the mixture is raised to 3.5 l by adding more water, and then the mixture is heated at 50° C. for 1 hr. The precipitate which is formed is cooled to room temperature, filtered, and added to 3.5 l of water. The pH of the water is adjusted to about 8 with ammonium hydroxide, and the resulting mixture is heated at 90° C. for 1 hr. The precipitate is cooled to room temperature, filtered, washed three times with 2 l of water, and refiltered. The precipitate is thereafter dried at 125° C. overnight to form titania containing surface hydroxyl groups. A portion of the hydroxylated titania (6 g) is stirred with 100 ml of 1N sulfuric acid for 1 hr, filtered, dried at 110° C. and heated at 500° C. for 3 hr to yield a sulfated titanium oxide solid superacid catalyst. The acid strength $H_0$ of sulfated titanium oxide is $\leq -14.52$. (M. Hino and K. Arata, Journal of the Chemical Society, Chem. Comm., 1979, 1148.)

EXAMPLES E-1 to E-4

Evaluation of Catalysts in the Synthesis of 9,9-Bis(4-hydroxyphenyl)fluorene

The following general procedure is employed for preparing 9,9-bis(4-hydroxyphenyl)fluorene, BHPF, whose structure is represented hereinbelow:

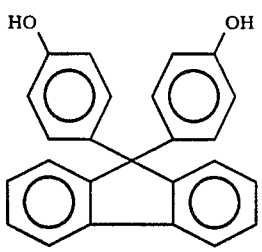

To a stirred mixture of fluorenone (5.8 g, 31.6 mmol, 98% purity), phenol (12 g, 127 mmol), and 3-mercaptopropionic acid (0.2 ml) is added catalyst all at once. The reaction mixture is stirred and heated to 95° C. over 60 min. The reaction mixture is analyzed by gas chromatography on a Hewlett Packard 5890 Series II Gas Chromatograph with a J&W DB-5 capillary column (15 m ×0.25 m). Process conditions and results are set forth in Table I for each catalyst E-1 through E-4.

In the process employing catalyst E-1, the solid product cake is digested with 150 ml of boiling toluene. The insoluble catalyst is filtered off, and the recovered catalyst is regenerated by drying at 150° C. in a vacuum oven for 16 hr. Thereafter, the regenerated catalyst is run a second time in the condensation process. The catalyst is recovered, regenerated and rerun in the condensation process a third and fourth time. After the fourth run, the catalyst is recovered, regenerated by drying for 16 hr at 150° C. in a vacuum oven, and then calcined at 600° C. under air. The regenerated and oxidized catalyst is rerun in the condensation process a fifth time. Process conditions and results for the regenerated catalysts are also set forth in Table I.

ered, weighing after drying 7 g (mp 222°-224° C., GC purity 99.4 percent; 63 percent yield). Impurity by-product is the o,p-isomer. The mother liquor is combined with 40 ml of water and rotary evaporated at 70°-80° C. to remove excess phenol. The combination with water and rotary evaporation are repeated twice more to obtain a colorless residue. Addition of 30 ml of water and stirring for 30 min at room temperature provides an additional crop of 4,4'-isomer (2.8 g; 97 percent purity) which is recovered by filtration. The combined, isolated yield of the 4,4'-isomer of BHPF is 88 mole percent. In a similar manner, isolated yields are obtained for the $2^{nd}$ through $5^{th}$ runs employing catalyst E-1 and for the runs employing catalysts E-2, E-3 and E-4.

EXAMPLE E-5

Preparation of 9,9-Bis(4-hydroxy-3-methylphenyl)fluorene

The following procedure is employed to prepare 9,9-bis(4-hydroxy-3-methylphenyl)fluorene, which may be represented by the following structure:

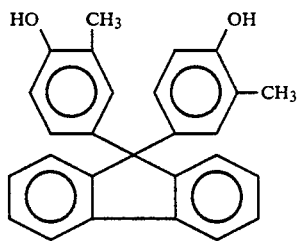

To a stirred mixture of fluorenone (18 g; 0.1 mole), o-cresol (57.5 g, 0.53 mole), and sulfated zirconium

TABLE I

| | | | | | | | Selectivity GC Area % | | | Isolated Yield Mole % |
|---|---|---|---|---|---|---|---|---|---|---|
| Ex. | Catalyst Description | Phenol Cmpd | g Catalyst | T, °C. | Time hr | % Conv Ketone | 4,4' | 2,4' | Ketal | BHPF |
| E-1 | ZrO(OH)$_2$/SO$_4$ | | | | | | | | | |
| E-1 | ZrO(OH)$_2$/SO$_4$ 1st run | Phenol | 7.5 | 90 | 1.0 | 99 | 97.1 | 2.6 | 0.4 | 88 |
| E-1 | ZrO(OH)$_2$/SO$_4$ 2nd run | Phenol | 7.0 | 87 | 1.5 | 98 | 97.1 | 2.2 | 0.7 | 85 |
| E-1 | ZrO(OH)$_2$/SO$_4$ 3rd run | Phenol | 6.3 | 95 | 2.0 | 99 | 96.5 | 2.6 | 0.8 | 89 |
| E-1 | ZrO(OH)$_2$/SO$_4$ 4th run | Phenol | 5.8 | 100 | 2.0 | 99 | 97.1 | 2.6 | 0.4 | 85 |
| E-1 | ZrO(OH)$_2$/SO$_4$ 5th run | Phenol | 5.2 | 85 | 1.5 | 99 | 98.1 | 1.3 | 0.6 | 85 |
| E-2 | ZrO$_2$/SO$_4$ | Phenol | 7.0 | 85 | 2.0 | 98 | 97.1 | 2.5 | 0.5 | 87 |
| E-3 | ZrOSi$_2$O$_5$/SO$_4$ | Phenol | 6.4 | 80 | 2.5 | 99 | 97.6 | 2.0 | 0.4 | 90 |
| E-4 | TiO$_2$/SO$_4$ | Phenol | 7.0 | 95 | 3.0 | 89 | 95.0 | 4.0 | 1.0 | 76 |
| E-5 | ZrO(OH)$_2$/SO$_4$ | o-Cresol | 15 | 85 | 2.0 | 95 | 98.0 | 1.8 | 0.2 | 87 |
| E-6 | ZrO(OH)$_2$/SO$_4$ | o-Fluorophenol | 15 | 85 | 2.5 | 97 | 98.4 | 1.2 | 0.4 | 90 |
| E-7[1] | ZrO(OH)$_2$/SO$_4$ | Phenol | 12 | 85 | 2.0 | 95 | 98.0 | 1.8 | 0.2 | 75 |
| E-8 | SrO$_2$/SO$_4$ | Phenol | 12 | 93 | 2.0 | 98 | 97.7 | 1.5 | 0.8 | 86 |
| E-9 | Zr(SO$_4$)$_2$ | Phenol | 12 | 93 | 2.0 | 99 | 95.0 | 2.5 | 2.5 | 83 |
| E-10 | WO$_3$/ZrO$_2$ | Phenol | 12 | 85 | 2.0 | 98 | 97.3 | 1.5 | 1.2 | 89 |

[1]Substrate is 2,7-dichlorofluorenone.

It is seen that the solid superacid catalysts E-1 through E-4 catalyze the condensation of phenol with fluorenone to the 4,4'-isomer of BHPF in high selectivity and high yield. It is seen that the ketone conversion is nearly quantitative at temperatures between 80° C. and 100° C. after only 1-3 hr. Very little of the 2,4'-isomer and by-product ketal are formed. It is also seen that the catalysts are easily recovered from the product mixture and regenerated. Regenerated catalysts also show high activity and selectivity.

The filtrate collected from the filtration of the catalyst E-1 (1$^{st}$ run) hereinabove is stirred overnight. Colorless crystals of the 4,4'-isomer of BHPF are recovoxyhydroxide catalyst E-1 (15 g) is added 0.3 ml of 3-mercaptopropionic acid. The mixture is stirred and heated at 85° C. for 3 hr. Analysis by gas chromatography gives the results set forth in Table I. It is seen that the sulfated zirconium oxyhydroxide catalyst is capable of catalyzing the condensation of fluorene with cresol, the cresol conversion being greater than 95 percent and the selectivity for 9,9-bis(4-hydroxy-3-methylphenyl)-fluorene being 98 mole percent.

The reaction mixture is cooled, and 100 ml each of toluene and water are added. The catalyst is filtered off. The filtrate is concentrated on a rotary evaporator to remove an o-cresol/water azeotropic mixture. Water, 100 ml, is added to the residue, and the o-cresol/water azeotrope is distilled off a second time. The addition of water and distillation are repeated two more times, and then the residue is dissolved in 100 ml of boiling toluene. On cooling, 9,9-bis(4-hydroxy-3-methylphenyl)fluorene crystallizes as white crystals which are separated by filtration and washed with hexane (29.9 g; mp 214°–217° C.; 79 mole percent isolated yield). Concentration of the filtrate provided a second crop of product (3.0 g) for a total isolated yield of 87 mole percent; GC purity is greater than 99 percent.

EXAMPLE E-6

Preparation of 9,9-Bis(3-fluoro-4-hydroxyphenyl)fluorene

The following procedure is employed to prepare 9,9-bis(3-fluoro-4-hydroxyphenyl)fluorene, which may be represented by the following structure:

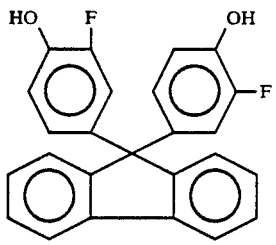

In a manner similar to Example E-5, starting from fluorenone (18 g, 0.1 mole), 2-fluorophenol (56 g, 0.5 mole), 3-mercaptopropionic acid (0.3 ml), and sulfated zirconium oxyhydroxide catalyst E-1 (15 g), 9,9-bis(3-fluoro-4-hydroxyphenyl)fluorene was isolated as a colorless solid in a 90 mole percent yield. (Mp 219°–221° C., GC purity 99.3 percent). Process conditions, conversion and selectivity are set forth in Table I.

EXAMPLE E-7

Preparation of 2,7-Dichloro-9,9-Bis(4-hydroxyphenyl)fluorene

The following procedure is employed to prepare 2,7-dichloro-9,9-bis(4-hydroxyphenyl)fluorene, which may be represented by the following structure:

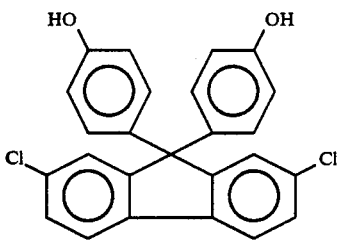

2,7-Dichlorofluorenone (15 g, 0.06 mole), phenol (37.6 g, 0.4 mole), 3-mercaptopropionic acid (0.3 ml), and sulfated zirconium oxyhydroxide catalyst E-1 (12 g), were contacted as in Example E-1. Product residue was recrystallized from a mixture of dimethylformamide and water to yield a solid identified as 2,7-dichloro-9,9-bis(4-hydroxyphenyl)fluorene. Isolated yield, 19.5 g; 75 mole percent; Mp 289°–292° C.; GC purity 99 percent. Process conditions, conversion and selectivity are set forth in Table I.

Preparation of Zirconium Sulfate Supported on Zirconia Catalyst (E-8)

Zirconium oxychloride ($ZrOCl_2.8H_2O$, 590 g) is dissolved in 2 l of water, and the resulting solution is heated to 80° C. An aqueous solution of ammonium hydroxide (2 l of 10N $NH_4OH$) is added to the zirconium oxychloride solution at a rate of 100 cc/min. A precipitate forms, and the precipitate and mother liquor are stirred for 1 hr at 80° C. The mixture is cooled to room temperature and filtered. The precipitate is washed with water until the washings give a pH of about 7–8. The washed precipitate is dried at 100° C. overnight to yield zirconium oxyhydroxide.

Zirconium oxyhydroxide (8.7 g, 40+mesh) is treated by immersion for 1 hr with occasional stirring in an aqueous solution of zirconium sulfate (3.25 g in 100 ml $H_2O$ heated to 25° C.). Then, the treated solid is filtered, but not rinsed. The solid is heated at 100° C. for 1 hr, then at 600° C. for 3 hr in air to yield a zirconia-supported zirconium sulfate superacid catalyst, $Zr(SO_4)_2$/$ZrO_2$. The acid strength $H_O$ of zirconium sulfate is $\leq -13.60$. (K. Arata, Advances in Catalysis, Vol 3., Academic Press, 1990.)

EXAMPLE E-8

Preparation of 9,9-Bis(4-hydroxyphenyl) fluorene

The zirconium sulfate/zirconia catalyst E-8 prepared hereinabove is tested in the reaction of phenol with fluorenone according to the procedure of Example E-1 with the results shown in Table I. It is seen that the conversion of phenol is 98 percent, and the selectivity to 4,4'-BHPF is 97.7 mole percent. Isolated yield of 4,4'-BHPF is 86 mole percent.

EXAMPLE E-9

Preparation of 9,9-Bis(4-hydroxyphenyl) fluorene

Zirconium sulfate (30.3 g) is heated in air at 125° C. for 1 hr, then at 300° C. for 1 hr, and then at 600° C. for 3 hr. The X-ray diffraction pattern of the material is consistent with a mixture of beta and gamma $Zr(SO_4)_2$. The acid strength $H_O$ of zirconium sulfate is $\leq -13.60$ (K. Arata, Advances in Catalysis, Vol 3., Academic Press, 1990.). The material is tested as a catalyst in the reaction of phenol with fluorenone as in Example E-1 and with the results shown in Table I. It is seen that the conversion of phenol is 99 percent, and the selectivity to 4,4'-BHPF is 95 mole percent. Isolated yield of 4,4'-BHPF is 83 mole percent.

Preparation of Tungsten Oxide/Zirconia Catalyst (E-10)

Zirconium oxychloride (155.03 g) is dissolved in 2 liters of water and the suspension is heated to 80° C. Two liters of 5N ammonium hydroxide are added to the zirconium oxychloride solution at a rate of 100 cc/min. The resulting precipitate and mother liquor are heated at 80° C. for 1 hr. The precipitate is filtered and washed 5 times. The filtercake is dried overnight at 110° C., crushed and sieved through 40 mesh screen to yield zirconium hydroxide, $Zr(OH)_4$. The zirconium hydroxide (33.7 g) is impregnated with an aqueous solution of ammonium metatungstate prepared by dissolving 5.54 g of $(NH_4)_6H_2W_{12}O_{40}$ in 15 cc of water. The tungsten oxide-impregnated zirconium hydroxide is dried at 120° C. for 1 hr. The dried material is then heated in air to 800° C. and held at that temperature for 3 hr to yield a tungsten oxide-zirconium oxide solid superacid catalyst, $WO_3/ZrO_2$. The acid strength $H_O$ of this superacid is $\leq -14.52$ (K. Arata, *Advances in Catalysis*, Vol. 37, 1990, p 20).

EXAMPLE E-10

Preparation of 9,9-Bis(4-hydroxyphenyl) fluorene

The tungsten oxide-zirconium oxide solid superacid E-10 (12 g), prepared hereinabove, is tested as a catalyst in the reaction of phenol with fluorenone under the following conditions: phenol (22.6 g, 240 mmol), fluorenone (5.4 g, 30 mmol), 3-mercaptopropionic acid (0.2 ml), heated at 85° C. for 2 hr. Results are set forth in Table I. It is seen that the conversion of fluorenone is 98 percent, and the selectivity to 4,4'-BHPF is 97.3 mole percent.

The reaction mixture is diluted with 50 ml of toluene and stirred at 85° C. for 10 min. Thereafter, the catalyst is filtered off, and the filtered catalyst is washed twice with 20 ml portions of toluene. The combined filtrates are mixed with 50 ml water, rotary evaporated to distill off the phenol-water azeotrope along with some toluene. The addition of water and the distillation are repeated twice more to provide a pale yellow solid. The solid is recrystallized from toluene providing 9.3 g of 9,9-bis(4-hydroxyphenyl)fluorene in an isolated yield of 89 mole percent (mp 222°-224° C., purity 99 percent by hplc).

What is claimed is:

1. A process of preparing a bishydroxy aromatic compound comprising contacting an aliphatic, alicyclic, alkaryl, or aromatic ketone with unsubstituted or substituted phenol, provided that the ketone does not further contain a carboxylic acid or aldehyde functionality and provided that the substituted phenol is not substituted with a cyano, nitro, caroxylic acid, or aldehyde functionality, the contacting occurring in the presence of a mercaptan cocatalyst and a solid superacid catalyst selected from the group consisting of metal sulfates, sulfated metal oxides, sulfated metal oxyhydroxides, sulfated metal oxysilicates, superacid metal oxides, and mixtures thereof, the superacid catalyst being characterized as having an acid strength $H_O$ stronger than about $-13.0$, and the contacting of the ketone with the phenol being conducted under reaction conditions such that a bishydroxy aromatic compound is formed.

2. The process of claim 1 wherein the ketone is an aromatic ketone.

3. The process of claim 2 wherein the aromatic ketone is represented by the formula:

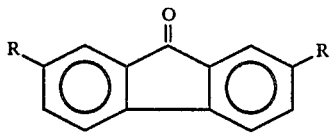

wherein each R may independently be hydrogen, alkyl having from 1 to about 5 carbon atoms, or halo.

4. The process of claim 3 wherein each R is hydrogen, and the ketone is fluorenone.

5. The process of claim 1 wherein the phenol is unsubstituted phenol.

6. The process of claim 1 wherein the phenol is a substituted phenol and the substituent is an alkyl moiety having from 1 to about 10 carbon atoms or a halo moiety.

7. The process of claim 1 wherein the molar ratio of the phenol to the ketone ranges from about 2 to about 40.

8. The process of claim 1 wherein the mercaptan cocatalyst is selected from the group consisting of ethylmercaptan, n-butylmercaptan, 1-octylmercaptan, 1-dodecylmercaptan, mercaptoethanol, mercaptoacetic acid, mercaptopropionic acid, mercaptoethanesulfonic acid, and mercaptopropanesulfonic acid.

9. The process of claim 8 wherein the mercaptan is 3-mercaptopropionic acid.

10. The process of claim 1 wherein the mercaptan is employed in a concentration between about 0.002 and about 0.5 mole mercaptan per mole ketone.

11. The process of claim 1 wherein the solid superacid catalyst is a sulfate, sulfated oxide, sulfated oxyhydroxide, or sulfated oxysilicate of zirconium, titanium, hafnium, aluminum, or tin, or a mixture thereof.

12. The process of claim 11 wherein the solid superacid catalyst is zirconium sulfate, sulfated zirconium oxide, sulfated zirconium oxyhydroxide, sulfated zirconium oxysilicate, or supported zirconium sulfate.

13. The process of claim 1 wherein the catalyst is a tungsten-zirconium oxide, tungsten-titanium oxide, molybdenum-zirconium oxide, molybdenum-titanium oxide, or a mixture thereof.

14. The process of claim 1 wherein the temperature is in the range from about 30° C. to about 200° C.

15. The process of claim 1 wherein the pressure ranges from about atmospheric to about 50 atm.

16. The process of claim 1 wherein the reaction is conducted in a fixed, bed continuous flow reactor at a flow rate between 0.1 hr$^{-1}$ and 10 hr$^{-1}$.

17. The process of claim 1 wherein the bishydroxy aromatic compound is represented by the formula:

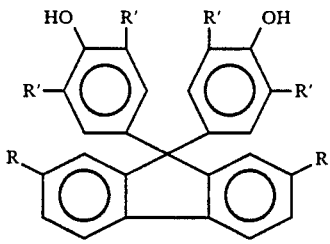

wherein each R is independently hydrogen, an alkyl group having from 1 to about 5 carbon atoms, or a halo group, and each R' is independently hydrogen, an alkyl group having from 1 to about 10 carbon atoms, or a halo group.

18. The process of claim 17 wherein each R and R' is hydrogen, and the bishydroxy aromatic compound is 9,9-bis(4-hydroxyphenyl)fluorene.

19. The process of claim 1 wherein the 4,4'-isomer of 9,9-bis(hydroxyphenyl)fluorene is isolated in a yield equal to or greater than about 85 mole percent.

20. A process of preparing 9,9-bis-(4-hydroxyphenyl)fluorene comprising contacting fluorenone and unsubstituted phenol in a phenol/fluorenone molar ratio ranging from 2 to about 40 in the presence of a mercaptan cocatalyst in a concentration ranging from 0.002 to about 0.4 mole mercaptan per mole ketone and in the presence of a solid superacid catalyst selected from the group consisting of metal sulfates, sulfated metal oxides, sulfated metal oxyhydroxides, sulfated metal oxysilicates, and metal oxides, the solid superacid catalyst being characterized as having an acid strength $H_0$ stronger than about $-13.0$, the contacting being conducted at a temperature between about 30° C. and 200° C. and a pressure between about atmospheric and 50 atm such that 9,9-bis-(4-hydroxyphenyl)fluorene is formed.

* * * * *